United States Patent [19]

Held et al.

[11] Patent Number: 5,035,858
[45] Date of Patent: Jul. 30, 1991

[54] METHOD FOR DISINFECTING MEDICAL MATERIALS

[75] Inventors: Jeffery S. Held, Chicago; James W. Sharp, Arlington Heights, both of Ill.

[73] Assignee: Stericycle, Inc., Rolling Meadows, Ill.

[21] Appl. No.: 530,438

[22] Filed: Jun. 1, 1990

Related U.S. Application Data

[63] Continuation of Ser. No. 421,332, Oct. 13, 1989, abandoned.

[51] Int. Cl.$^5$ .......................... A61L 2/04; A61L 2/08; A61L 2/12
[52] U.S. Cl. .................................. 422/21; 422/291; 422/292; 422/27; 378/64
[58] Field of Search ........................ 422/21, 22, 24, 20, 422/32, 44, 291, 307, 292, 297, 27; 378/64

[56] References Cited

U.S. PATENT DOCUMENTS

| | | | |
|---|---|---|---|
| 2,114,345 | 4/1938 | Hayford | 175/311 |
| 2,731,208 | 1/1956 | Dodd | 241/41 |
| 3,095,359 | 6/1963 | Heller | 435/30 |
| 3,215,539 | 11/1965 | Landy | 99/221 |
| 3,490,580 | 1/1970 | Brumfield et al. | 206/63.2 |
| 3,494,723 | 2/1970 | Gray | 21/54 |
| 3,547,577 | 11/1968 | Lovercheck | 422/34 |
| 3,551,090 | 12/1970 | Brumfield et al. | 21/54 |
| 3,602,712 | 8/1971 | Mann | 250/44 |
| 3,617,178 | 11/1971 | Clouston | 21/0.2 |
| 3,704,089 | 11/1972 | Stehlik | 21/54 |
| 3,753,651 | 8/1973 | Boucher | 422/21 |
| 3,885,915 | 5/1975 | Utsumi et al. | 21/54 |
| 3,940,325 | 2/1976 | Hirao | 204/159.2 |
| 3,948,601 | 4/1976 | Fraser | 21/54 R |
| 3,958,936 | 5/1976 | Knight | 21/93 |
| 4,140,537 | 2/1979 | Luck | 106/155 |
| 4,151,419 | 4/1979 | Morris et al. | 378/69 |
| 4,250,139 | 2/1981 | Luck | 422/21 |
| 4,457,221 | 7/1984 | Geren | 99/451 |
| 4,524,079 | 6/1985 | Hofmann | 926/234 |
| 4,563,259 | 1/1986 | Rayner | 524/99 |
| 4,569,736 | 2/1986 | Kosegake | 523/105 |
| 4,599,216 | 7/1986 | Rohrer | 422/21 |
| 4,620,908 | 11/1986 | Van Duzer | 204/157.68 |
| 4,652,763 | 3/1987 | Nablo | 250/492.3 |
| 4,671,935 | 6/1987 | Rohrer | 422/21 |
| 4,775,770 | 10/1988 | Fritz | 219/10.55 |
| 4,801,427 | 1/1988 | Jacob | 422/23 |
| 4,808,782 | 2/1989 | Nakagawa et al. | 219/10.55 |
| 4,808,783 | 2/1989 | Stenstrom | 219/10.55 |
| 4,818,488 | 4/1989 | Jacob | 422/23 |
| 4,917,586 | 4/1990 | Jacob | 422/21 |
| 4,931,261 | 6/1990 | Jacob | 422/292 |

FOREIGN PATENT DOCUMENTS

| | | | |
|---|---|---|---|
| 3710156 | 10/1988 | Fed. Rep. of Germany . | |
| 1123705 | 11/1984 | U.S.S.R. | 422/22 |
| 942374 | 8/1962 | United Kingdom | 422/21 |
| 1406789 | 9/1975 | United Kingdom | 422/21 |

OTHER PUBLICATIONS

Christensen et al., "The Multi-Medical Equipment" 1972, pp. 345-354.
Morganstern, "The Future of Radiation Sterilization", Apr. 28, '77, pp. 1-26.
Reynolds et al., "Thermoradiation Inactivation of Naturally Occurring Bacterial Spores in Soil," *Applied Microbiology*, vol. 28 (3), pp. 406-410, Sep. 1974.
Brannen, "A Kinetic Model for the Biological Effects of Ionizing Radiation," Report No. SAND74-0269, Sandia Laboratories, Albuquerque, New Mexico, Printed Oct. 1974.
1976 Progress Report–"Beneficial Uses Program–Period Ending Dec. 31, 1976," Report No. SAND77-0426, Sandia Laboratories, Albuquerque, New Mexico, Printed Mar. 1977.
Sivinski, "General Description of the Sludge Irradiation Process," pp. 57-68, National Symposium on the Use of Cesium-137 to Process Sludge for Further Reduction of Pathogens, Held in Denver, Colorado, Sep. 3-4, 1980, Published Dec. 1980.
Report on "Electromagnetic Radiation and Ionizing Energy," unknown source and publication date.
Tonetti, "Disease Control Requirements for Various Sludge Use," pp. 43-56, National Symposium on the Use of Cesium-137 to Process Sludge for Further Reduction of Pathogens, held in Denver, Colo., Sep. 3-4, 1980, published Dec. 1980.
Ward, "Molecular Mechanisms of Radiation-Induced Damage to Nucleic Acids," Unknown Source and Publication Date.
Markitanova et al., Study of Reagentless Sterilization of Waste Waters. Journal of Applied Chemistry of the USSR. vol. 59, No. 11, pp. 2561-2564, Nov. 1986.
Chipley, Effects of Microwave Irradiation on Microorganisms. Advances in Applied Microbiology, vol. 26, pp. 129-145, 1980.

(List continued on next page.)

*Primary Examiner*—Edward P. Westin
*Assistant Examiner*—Don Wong
*Attorney, Agent, or Firm*—Willian Brinks Olds Hofer Gilson & Lione

[57] ABSTRACT

A method of disinfecting medical materials, which comprises heating medical materials and exposing the medical materials to gamma radiation, is provided. One method of heating is the application of radio-frequency waves. The medical materials are subjected to radio-frequency waves for at least approximately 5 minutes and to gamma radiation measuring at least approximately 0.25 Mrads. When the starting material consists of presorted medical or veterinary waste, the method further comprises shredding the irradiated waste and recycling the shredded waste.

24 Claims, No Drawings

OTHER PUBLICATIONS

Center for Materials Fabrication, Dielectric Heating, RF & Microwave. TechCommentary, vol. 4, No. 1, pp. 2–4, 1987.

Serota, Heating with Radio Waves, Automation, Sep. 1973.

Stephan K. Hall, "Infectious Waste Managements: A Multi-Faceted Problem," Pollution Engineering, 74–78 (Aug. 1989).

N.Y. Times, "Science Watch: Microwave Sterilizer is Developed," (Jun. 20, 1989).

Bill Paul, "Combustion Says Firm Sterilizes Medical Waste with Microwaves," The Wall Street Journal, p. B3 (Apr. 10, 1989).

United States Pharmacopoeia XX: Section 1211, "Sterilization," pp. 1037–1040.

METHOD FOR DISINFECTING MEDICAL MATERIALS

This application is a continuation of application Ser. No. 421,332, filed Oct. 13, 1989 now abandoned.

BACKGROUND OF THE INVENTION

The present invention relates generally to a method of disinfecting medical materials and more particularly to a method of disinfecting medical materials by exposing the materials to a combination of heat and gamma radiation. The term medical materials encompasses medical waste, veterinary waste and medical products. The problems with current waste handling methods will be discussed first.

The problem of disposal of solid waste is becoming increasingly acute. The primary methods of solid waste disposal have been burning or burial in landfills. These two methods have severe disadvantages. Burning liberates waste particles and fumes which contribute to acid rain. Burying wastes results in toxic chemicals leaking into the surrounding earth and contaminating the water supply. Although increasing amounts of solid waste are being recycled, which alleviates the problems of the other two disposal methods, presently available recycling methods do not provide a complete solution to the disposal problem.

Waste disposal is of even more urgent concern when the waste may cause infection. Such infectious waste is a by-product of medical and veterinary care. For example, regulated medical waste consists of the following categories:

1. Cultures and stocks of infectious agents and associated biologicals,
2. Pathological wastes,
3. Human blood and blood products,
4. Contaminated sharps (including needles, syringes, blades, scalpels, and broken glass),
5. Animal waste,
6. Isolation waste (gloves and other disposable products used in the care of patients with serious infections), and
7. Unused sharps.

These wastes can be generally divided between general medical waste, including waste listed above in categories 1, 2, and 3; veterinary waste, or category 5; and waste that is predominantly plastic, including categories 4 and 6. Hospitals typically segregate types of waste. Contaminated sharps and isolation waste are categories of special concern, as this waste may carry highly dangerous infections such as AIDS or hepatitis. Sharps in particular have caused public panic when observed on beaches and other public areas.

Hospitals and other generators of medical and veterinary waste employ three main methods of waste handling: 1) on-site incineration of the waste, 2) on-site steam autoclaving of the waste and later shipment to a landfill, and 3) no on-site processing before turning the waste over to a waste hauler.

Predominantly located in urban areas, many hospital incinerators emit pollutants at a relatively high rate. In the emissions of hospital incinerators, the Environmental Protection Agency (EPA) has identified harmful substances, including metals such as arsenic, cadmium, and lead; dioxins and furans; organic compounds like ethylene, acid gases, and carbon monoxide; and soot, viruses, and pathogens. Emissions from these incinerators may be a bigger public health threat than improper dumping. (Stephen K. Hall, "Infectious Waste Management: A multi-faceted Problem," Pollution Engineering, 74-78 (Aug. 1989)).

Although steam autoclaving may be used to disinfect waste before further processing, it is expensive and time-consuming. Temperature monitoring devices such as thermocouples and biological indicators such as heat-resistant *Bacillus stearothermophilus* spores may be used to assure effective disinfection. The application of heat denatures the protein in microorganisms causing death in a short time. Viruses are rapidly inactivated; bacteria and particularly bacterial spores survive somewhat longer than viruses.

U.S. Pat. No. 2,731,208 (Dodd) teaches a steam-sterilizing apparatus for disposing of contaminated waste which incorporates shredding the waste ("including paper containers such as used sputum cups," Col. 1, Lines 28-29). This reference teaches processing only limited types of items; it teaches the use of steam sterilization alone and has the further disadvantage of depositing the shredded mixture into a sewer. (Col. 4, line 49).

Whether or not the hospital first autoclaves its medical waste, including broken needles and glass, the waste is then turned over to a waste handler for transport to a landfill or other depository. U.S. Pat. No. 3,958,936 (Knight) teaches compaction of hospital waste for more efficient landfill disposal. Specifically, this reference teaches the application of heat in the range of about 400° to 600° F. to hospital and other waste to melt the plastic and turn it into a hard, compact block for safer disposal in landfills. The waste is disinfected and needles become imbedded in the plastic. This method has the disadvantages of requiring high temperatures and landfill disposal. As mentioned above, metropolitan landfills are becoming filled and unauthorized dumping is becoming a problem.

Another area of concern is the sterilization of medical products. By medical product we mean any product which must be disinfected or sterilized prior to use in patient or animal care. This area is exemplified by, but not limited to, the following: needles, syringes, sutures, scalpels, gloves, drapes, and other disposable items. Many reusable items also must be provided in sterile form. Primary sterilization methods include the use of autoclaving, ethylene oxide, and ionizing radiation. The heat and humidity of autoclaving are quite damaging to many disposable medical products; hence autoclaving is not preferably used, and ethylene oxide and ionizing radiation are preferred commercially.

To sterilize medical products with known methods, poisonous ethylene oxide gas fills a closed chamber containing the products to be sterilized. For effective sterilization, not only must the ethylene oxide concentration be carefully controlled, but the temperature, humidity and porosity of the sterilizer load also must be regulated. Ethylene oxide is slow to dissipate from plastics and may require that the medical products be stored until the ethylene oxide falls to a safe level. Ethylene oxide also must be carefully vented to the atmosphere after the sterilization cycle to avoid poisoning workers.

If ionizing radiation such as gamma radiation is used by itself, it must be administered at such intense doses that many plastics become yellow and brittle. For example, U.S. Pat. No. 3,940,325 (Hirao) teaches ways to adjust the formulas of plastics for syringes to avoid yellowing and cracking after exposure to gamma radiation. Other substances may also be damaged by radiation.

Ionizing radiation, or gamma radiation, is produced by electron accelerators or radioisotopes such as cobalt 60 or cesium 137. Both sources produce high-energy photons which disinfect by inactivating the DNA of viruses and bacteria. These irradiated microorganisms lose their ability to reproduce and cause infections. Gamma radiation rapidly inactivates bacteria but is less effective against viruses. On a large-scale industrial basis, gamma irradiation with cobalt 60 has been used to sterilize medical products prior to their use in patients. The dosage of gamma radiation, measured in rads or megarads (Mrads), varies but a dose of 2.5 Mrads is usually selected as a starting point in known methods. However, such doses also damage the product being sterilized. The following patents teach methods to sterilize medical products with less harm to the product.

U.S. Pat. No. 3,617,176 (Clouston) teaches a method of improving sterilization efficiency by increasing hydrostatic pressure. Elevated hydrostatic pressure causes sterilization-resistant bacterial spores to germinate or begin to grow, but it has no effect on viruses. Germination makes the bacteria more sensitive to radiation. This reference teaches optimizing the hydrostatic pressure effect by adjusting temperature (up to 80° C.), and then disinfecting the sutures with lower doses of gamma radiation or other modes of disinfection. According to Clouston, elevated pressure and fluid or moist gas are essential to his method; raised temperature alone has a negligible effect. Furthermore, the pressure/heat/moisture treatment this reference teaches is intended to cause bacterial spores to germinate, not to immediately sterilize or inactivate microorganisms.

In contrast, U.S. Pat. Nos. 4,620,908 (Van Duzer) and 3,704,089 (Stehlik) teach pre-freezing injectable proteins and surgical adhesive respectively before irradiation with cobalt 60. In these methods, the temperature is reduced not to sterilize the product, but to protect the product from damage by gamma radiation.

U.S. Pat. No. 3,602,712 (Mann) describes an apparatus for gamma irradiation and disinfection of sewage and industrial waste. Gamma radiation by itself, however, is impractical for disinfecting medical waste. Gamma radiation in the doses used to sterilize medical products is considered too expensive for medical waste processing.

Besides gamma radiation, other energy sources are being considered as potential sterilants in known systems. Microwaves are increasingly being investigated for rapid sterilization of individual medical devices and shredded medical waste. Recently, an experiment showed that metallic instruments could be disinfected in only 30 seconds in a microwave. (*N. Y. Times*, "Science Watch: Microwave Sterilizer is Developed," June 20, 1989). A problem is that this particular method can handle only a few instruments at a time.

According to one publication, a medical waste disposal system utilizing microwaves has apparently been developed. This system first shreds the waste, sprays it with water and passes the mixture through a microwave chamber designed to raise the temperature of the mixture to 205° C. After the disinfection step, the system compresses the waste and packages it for shipment to landfills or incinerators. (*The Wall Street Journal*, p. B3, Apr. 10, 1989). One potential problem with this system is that shredding before disinfection could release infectious particles to the environment and may thus spread contagion. Another problem is ultimate disposal of the waste: It persists in landfills or may pollute the air when incinerated.

Further, microwaves are limited in their penetration. If applied to large-scale, boxed medical waste, the microwaves alone do not heat very effectively. In contrast, radio-frequency (R-F) waves are relatively low-frequency waves which penetrate more effectively. Radio-frequency waves have been used directly and indirectly for sterilization.

U.S. Pat. No. 2,114,345 (Hayford) teaches a radio-frequency applicator with electroscopic control for destroying bacteria in bottled beer and similar articles. This reference teaches an apparatus that sterilizes with radio-frequency waves alone. Therefore, it teaches away from the combination of radio-frequency waves with gamma radiation.

U.S. Pat. No. 3,948,601 (Fraser et al.) teaches the indirect use of radio-frequency waves in disinfecting a wide variety of medical and hospital equipment as well as human waste. This reference teaches the use of radio-frequency waves to heat certain gases (particularly argon) to ionize into gas plasma at approximately 100° to 500° C. This references teaches that "cool" plasma, (Col. 1, Line 12) reaches the article to be sterilized at a temperature of only 25° to 50° C. and very low pressure and effectively sterilizes the article. However, sterilization by plasma gas, does not suggest the direct use of radio-frequency waves in sterilization Reprocessing of waste and especially medical waste is vital for several reasons. First, landfills, particularly in many urban areas, are becoming filled. In addition, older landfills may leak. Thus, burying wastes is becoming more of a problem. Second, merely burning waste can pollute the atmosphere and cause acid rain. Current reprocessing technology should be employed to process medical waste for effective utilization.

What was needed before the present invention was a method to disinfect or destroy the infectious potential of medical waste and to dispose of it in a manner harmless to health care workers, waste handlers, and the public at large.

BRIEF SUMMARY AND OBJECTS OF THE INVENTION

The present invention provides a method of processing medical materials, such as medical and veterinary waste and medical products, which disinfects or sterilizes the material by a combination of heating and gamma radiating.

One step in the method comprises heating medical materials (for example with radio-frequency waves) to raise their internal temperature to at least 60° C., which is sufficient to inactivate most viruses. Another step comprises applying a reduced dose of gamma radiation to the material to complete the disinfection or sterilization process by inactivating other microorganisms, mostly bacteria.

The invention additionally comprises steps for further processing of pre-sorted medical and veterinary waste either as recycled plastic or as refused-derived fuel.

Therefore, in view of the foregoing, it is a primary object of the present invention to disinfect medical materials by heating the materials and exposing them to gamma radiation. A further object of the invention is to dispose of medical and veterinary waste in an environmentally safe manner.

Additional objects, advantages and novel features of the invention will be set forth in part in the description which follows, and in part will become apparent to those skilled in the art upon examination of the following or may be learned by practice of the invention. The objects and advantages of the invention may be obtained by means of the methods and combinations particularly pointed out in the appended claims.

DESCRIPTION OF THE PRESENTLY PREFERRED EMBODIMENTS

Disinfection

The present invention relates to a method for disinfecting medical materials. By medical materials, we mean medical and veterinary waste as well as medical products. Medical and veterinary wastes are disinfected, or rendered incapable of causing an infection. The present method inactivates microorganisms in medical and veterinary waste so that the waste can no longer cause an infection. Medical products are preferably sterilized, which completely kills all bacteria and viruses. Both disinfection and sterilization are accomplished by heating and applying gamma radiation.

Preliminary to the use of the present invention, medical material arrives at a processing and recycling facility. Preferably, the material is shipped in sealed containers. This means of shipping medical materials is known in the art and has the advantages that medical waste does not infect its handlers and that contamination of medical products in transit is minimized. At the facility the containers are preferably arranged on pallets and shrink-wrapped with plastic. The pallets are then moved into a heating chamber which could deliver heat by any of a variety of methods, such as radio-frequency, infrared and microwaves and electrical and gas radiant heating.

A preferred embodiment of this chamber is a tunnel configuration and means, such as a track, for moving the material through the tunnel. This arrangement permits the material to be gradually heated as it travels through.

The pallets are held in the heat chamber and exposed to the heat source for a sufficient time to raise the temperature of the medical materials to at least approximately 60° C. It will be recognized by those skilled in the art that temperatures as high as 170° C. may be used without adversely affecting the process.

Next, the pallets are moved into a shielded gamma irradiation chamber. The gamma chamber is insulated to prevent radiation from escaping into the environment. The same type of facility that is in current use for gamma irradiation of medical supplies may be used for this step. For example, a suitable gamma irradiator is Model #RT 4101, available from Radiation Technology, Inc., Rockaway, N.J. In the chamber, a core of radioactive matter (preferably cobalt 60) emerges from a liquid bath and emits ionizing radiation that is relatively constant during the period when any sample is being irradiated. For subsequent loads, the time is gradually increased to account for radioactive decay of the cobalt 60. Absorbed radioactivity is measured in rads. The amount to be delivered to medical materials is measured in megarads (Mrads), or millions of rads. Doses may range from as little as about 0.25 Mrads to as high as about 2.5 Mrads or more. It will be recognized by those skilled in the art that higher radiation doses will not adversely affect the process.

In one embodiment, the medical materials are moved along a trackway, through the heat chamber and the gamma-irradiation chamber. In this arrangement, the distance from radiation sources varies but is additive for the journey through each chamber. The total dose of radiation to which the waste is exposed during its dwell time in the chamber is planned to provide sufficient disinfection. With a track arrangement, the entrance and exit of the chambers are open but additional walls are arranged to block the escape of radiation into the surrounding areas Such chambers are in common use for cobalt 60 sterilization of medical products.

Validation

Preferably, a medical material disinfecting facility using the present invention is validated to assure the adequacy of the disinfection process. Validation may be performed when each facility is constructed and at intervals during its operation. Validation may consist of placing heat detecting devices such as thermocouples and/or known amounts of particular microorganisms which are resistant to heat and to gamma radiation respectively into a maximally loaded pallet of medical materials. Sufficient heat to raise the temperature of a sterilizer's load to about 60° C. and a gamma radiation dose of about 0.50 Mrads are delivered to the test pallet. If thermocouples are used, they should all record at least the minimum temperature of about 60° C. After the entire disinfection cycle is complete, the microorganism samples are removed from the pallet and cultured (given nutrients and other appropriate conditions for growth) to determine survival. A typical heat-resistant microorganism which may be used in validation is *Bacillus stearothermophilus*. A typical radiation-resistant microorganism is *Bacillus pumilus*. If more than 1 in 10,000 of either microorganism survives the timed cycles, the exposure to heat and/or gamma radiation is increased about 5%, or about 200,000 rads, and another pallet is tested.

Processing for Recycling

Another embodiment of the invention consists of starting with medical or veterinary waste that has been pre-sorted into containers of plastic and general medical waste, respectively. High-grade plastics are used in medical products and can be shredded and remolded into a variety of products. This waste is subjected to heat and gamma radiation as described above. Then the containers of disinfected plastic are moved to a "plastics" shredder. For example, an electrically powered shredder with pneumatic ram assist and negative pressure canopy reduces medical waste to small particles and is available as Model Dual 1000 E from Shredding Systems, Inc., Wilsonville, Oreg. The negative pressure canopy minimizes particles entering the surrounding air. The containers are opened and the disinfected plastic is placed in the shredder and shredded to particles of about one quarter to one half inch. This disinfected, shredded material is transferred into 55-gallon drums for shipment to re-users of plastic.

Likewise, the containers of disinfected general medical waste are moved to the "general medical waste" shredder. After the containers are opened, the general medical waste is placed in the shredder and shredded to particles of about one quarter to one half inch. The disinfected waste is placed in further containers. This waste contains a mixture of paper, plastic, and metal and can be used as fuel. Possible users include cement kilns which operate at temperatures of about 2,500° F. or more, and which would otherwise use high-sulfur coal. Because this general medical waste is low in sulfur, its use as fuel will decrease sulfur-caused acid rain.

Another preferred embodiment of this invention has a heat chamber which is a radio-frequency chamber having a tunnel configuration with the following approximate dimensions: 50 feet long, 20 feet wide and 20 feet high. The tunnel is lined with 3 mm-thick copper sheeting. The copper lining and the arrangement of the electrodes inside the tunnel are designed to confine the radio-frequency waves to the tunnel.

In the radio-frequency chamber, a system of exciter and ground electrodes generate electromagnetic waves in the radio-frequency band. The radio-frequency band is between audio and infrared frequencies and comprises approximately 10 hertz (Hz) to 300 gigahertz (GHz). When the electrode system is supplied with electricity, it launches an electromagnetic wave into the target medical materials.

The radio-frequency waves penetrate the pallets of medical materials. The medical materials absorb these waves whose energy is thought to produce heat by inducing dipole rotation and molecular vibration. When radio-frequency waves are absorbed, they may cause differential heating. Moist articles and metal objects absorb more waves and may create "hot spots," or uneven heating. In closed containers or boxes, the steam and heat from these objects are redistributed to the entire contents of the containers.

The pallets are held in the radio-frequency chamber and exposed to radio-frequency waves for a sufficient time to raise the temperature of the medical materials to at least approximately 60° C. It will be recognized by those skilled in the art that temperatures as high as 170° C. will not adversely affect the process. Preferably, the exposure to radio-frequency waves would last about 5 to 30 minutes. More preferably, the medical materials are exposed to the radio-frequency waves for approximately 12 minutes. However, the optimal time in the chamber and amount of radio-frequency waves for a particular facility will vary and may be determined as described in "Validation."

Another embodiment of the invention arranges the heating elements (for example, the radio-frequency generating system of exciters and grounds) inside the gamma radiation chamber for simultaneous exposure of the medical materials to heat or radio-frequency waves and gamma radiation.

Another embodiment of the invention orients the heat or radio-frequency chamber with respect to the gamma radiation chamber so that the medical material is first exposed to gamma radiation and then heated.

Another embodiment of the invention employs a system of tracks and/or conveyor belts to move medical or veterinary waste from the sterilization chambers to the shredders.

The foregoing descriptions of the preferred embodiments of the present invention have been presented for purposes of illustration and description. They are not intended to be exhaustive or to limit the invention to the precise forms disclosed, and obviously many other modifications and variations are possible in light of the above teachings. The embodiments were chosen and described to best explain the principles of the invention and its practical applications, thereby enabling others skilled in the art to best utilize the invention in its various embodiments and with various modifications as are suited to the particular use contemplated. It is intended that the scope of the invention be defined by the following claims, including all equivalents.

We claim:
1. A method of disinfecting medical materials comprising:
    (a) heating the medical materials to approximately 60° C.; and
    (b) exposing the medical materials to a gamma radiation dose of approximately 0.25 to 2.0 Mrads.
2. A method of disinfecting medical materials, as recited in claim 1, wherein the step of heating precedes the step of gamma irradiation.
3. A method of disinfecting medical materials, as recited in claim 1, wherein the step of gamma irradiation comprises exposing the medical materials to radioactive cobalt 60.
4. A method of disinfecting medical materials, as recited in claim 1, wherein the step of gamma irradiation comprises exposing the medical materials to radioactive cesium 137.
5. A method of disinfecting medical materials comprising:
    (a) irradiating the medical materials with radio-frequency waves to heat the materials to about 60° C.;
    (b) exposing the medical materials to gamma radiation in the range of about 0.25 megarads to about 2.0 megarads.
6. A method of disinfecting medical materials, as recited in claim 5, wherein the step of irradiating with radio-frequency waves precedes the step of irradiation with gamma radiation.
7. A method of disinfecting medical materials, as recited in claim 5, wherein the step of gamma irradiation comprises exposing the medical materials to radioactive cobalt 60.
8. A method of disinfecting medical materials, as recited in claim 5, wherein the step of gamma irradiation comprises exposing the medical materials to radioactive cesium 137.
9. A method of disinfecting and processing medical waste comprising:
    (a) heating medical waste to a temperature of approximately 60° C.;
    (b) exposing the heated medical waste to gamma irradiation in the range of about 0.25 megarads to about 2.0 megarads;
    (c) shredding the irradiated waste; and
    (d) recycling the shredded waste.
10. A method of disinfecting and processing medical waste, as recited in claim 9, wherein the step of shredding irradiated waste comprises reducing the materials to particles in a size range of approximately one quarter to one half inch.
11. A method of disinfecting and processing medical waste, as recited in claim 9, further comprising the step of pre-sorting the medical waste into plastics and general medical waste and placing the plastics and general medical waste into different containers for plastics and general medical waste respectively.
12. A method of disinfecting and processing medical waste, as recited in claim 11, wherein the recycling step for pre-sorted medical waste comprises reusing the plastic and using the general medical waste as fuel.
13. A method of disinfecting and processing medical waste, as recited in claim 9, wherein the step of gamma irradiation comprises exposing the medical waste to radioactive cobalt 60.

14. A method of disinfecting and processing medical waste, as recited in claim 9, wherein the step of gamma irradiation comprises exposing the medical waste to radioactive cesium 137.

15. A method of disinfecting medical materials comprising:
   (a) heating the medical materials to approximately 60° C.; and
   (b) exposing the medical materials to an ionizing radiation dose of approximately 0.25 to 2.0 megarads.

16. The method of disinfecting medical materials, as recited in claim 15, wherein the step of heating the medical materials comprises irradiating the medical materials with radio-frequency waves.

17. The method of disinfecting medical materials, as recited in claim 15, wherein the step of exposing the medical materials to ionizing radiation comprises irradiating with an electron accelerator or other machine source of radiation.

18. The method of disinfecting medical materials, as recited in claim 15, wherein the step of irradiating with radio-frequency waves precedes the step of irradiating with ionizing radiation.

19. The method of disinfecting medical materials, as recited in claim 15, further comprising the steps of
   (c) shredding the irradiated material; and
   (d) recycling the shredded material.

20. The method of disinfecting medical materials, as recited in claim 19, wherein the step of shredding irradiated material comprises reducing the materials to particles in a size range of approximately one quarter to one half inch.

21. The method of disinfecting medical materials, as recited in claim 19, further comprising the steps of
   (c) pre-sorting medical material into plastics and general medical material; and
   (d) placing the plastics and general medical waste into different containers for plastics and general medical material, respectively.

22. The method of disinfecting medical materials, as recited in claim 21, wherein the recycling step for pre-sorted medical materials comprises reusing the plastic and using the general medical material as fuel.

23. A method of disinfecting and processing medical waste comprising:
   (a) shredding the medical waste:
   (b) heating the shredded medical waste to a temperature of approximately 60° C.;
   (c) exposing the heated medical waste to gamma irradiation; and
   (d) recycling the irradiated medical waste.

24. A method of disinfecting medical waste comprising:
   (a) shredding the medical waste;
   (b) heating the shredded medical waste to a temperature of approximately 60° C.;
   (c) exposing the heated medical waste to an ionizing radiation dose of approximately 0.25 to 2.0 megarads; and
   (d) recycling the irradiated medical waste.

* * * * *